United States Patent [19]

Jozefowicz et al.

[11] Patent Number: 5,112,449
[45] Date of Patent: May 12, 1992

[54] TWO PHASE METAL/OXIDE FILMS

[75] Inventors: Mark A. Jozefowicz; Aron M. Rosenfeld, both of Kingston, Canada

[73] Assignee: Alcan International Limited, Montreal, Canada

[21] Appl. No.: 497,555

[22] Filed: Mar. 22, 1990

[30] Foreign Application Priority Data

Mar. 22, 1989 [CA] Canada ............................... 594495
Sep. 29, 1989 [CA] Canada ............................... 615000

[51] Int. Cl.$^5$ ..................... C25D 11/12; C25D 5/44
[52] U.S. Cl. ..................................... 205/175; 205/201
[58] Field of Search ................ 204/37.6, 38.3, 42, 204/56.1, 58

[56] References Cited

U.S. PATENT DOCUMENTS

| | | | |
|---|---|---|---|
| 3,953,625 | 4/1976 | Quaintance et al. | 427/258 |
| 4,310,586 | 1/1982 | Sheasby et al. | 204/42 |
| 4,472,533 | 9/1984 | Moskovitz | 502/320 |
| 4,687,551 | 8/1987 | Furneaux et al. | 204/11 |
| 4,837,061 | 6/1989 | Smits et al. | 428/40 |
| 4,921,823 | 5/1990 | Furneaux et al. | 502/4 |

FOREIGN PATENT DOCUMENTS

| | | |
|---|---|---|
| 0178831 | 4/1986 | European Pat. Off. |
| 3124522 | 1/1983 | Fed. Rep. of Germany |
| 53-22185 | 3/1978 | Japan |
| 60-33390 | 2/1985 | Japan |
| 60-177198 | 9/1985 | Japan |
| 1532235 | 11/1978 | United Kingdom |

Primary Examiner—John Niebling
Assistant Examiner—Kishor Mayekar
Attorney, Agent, or Firm—Cooper & Dunham

[57] ABSTRACT

A process for producing a two phase metal/oxide film. The process comprises forming a porous oxide film on a substrate, introducing a weakened stratum into the oxide film so that the film (or at least an outer part of the film) can be subsequently detached along the weakened stratum, depositing a metal on and/or within the pore of the film, and detaching at least the outer film part from the substrate. The detached film so produced can be used for many purposes depending on the film thickness, position of the metal deposits on or with the pores etc. Examples include optical interference devices, magnetic media, coatings for plastics and paper, etc.

10 Claims, 5 Drawing Sheets

TIO$_2$ AND Al$_2$O$_3$ BASED HEAT MIRROR SPECTRA

TWO PHASE METAL/OXIDE FILMS

This invention relates to two phase metal/oxide films. More particularly, the invention relates to porous oxide films supporting metal deposits.

Oxide films supporting metal deposits can be used for a variety of purposes, e.g. as catalysts for various chemical reactions, but it is difficult to produce such films in a highly controllable manner and at reasonable economic cost.

Accordingly it is an object of the present invention to provide a process for forming such films and to produce two phase films by the process.

According to one aspect of the invention, there is provided a process for producing a two phase metal/oxide film, which comprises forming a porous oxide film on a substrate, introducing a weakened stratum into the oxide film so that at least an outer part of the film can be subsequently detached along said stratum, depositing a metal on and/or within the pores of said film in at least said outer film part, and detaching at least said outer film part from said substrate.

According to another aspect of the invention there is provided a two phase metal/oxide film comprising a porous oxide film having a metal deposited on a surface of said film and/or with the pores of said film.

Other aspects of the invention relate to devices incorporating the two phase metal/oxide film mentioned above.

The most convenient way of forming a porous oxide film on a substrate is by porous anodizing a metal substrate made of an anodizable metal, e.g. aluminum or an anodizable aluminum alloy. This is done by carrying out the electrolysis in an electrolyte containing an acid, e.g. phosphoric acid, sulfuric acid or oxalic acid, which tends to partially dissolve the oxide film as it is being formed. Films of virtually any desired thickness can be grown by carrying out the electrolysis for a suitable period of time.

Porous anodization can also be modified to introduce the required weakened stratum into the oxide film. This is achieved by a pore branching technique as disclosed in our European patent application serial number 0 178 831 published on Apr. 23, 1986 (the disclosure of which is incorporated herein by reference) and involves a variation in the anodization voltage in a continuous or stepwise manner during the porous anodization step. This causes each pore formed during the normal anodization to branch out at its bottom part to form numerous smaller pores that collectively weaken the film. For example, the anodization voltage can be reduced from the normal anodization voltage (typically in the range of 3 to 200 V, but more usually 5 to 100 V) to 0 V in 0.5 V increments. We have found that the introduction of the weakened stratum in this way can be carried out without causing the film to separate prematurely from the substrate.

A metal can be deposited within the pores of the film and/or on the outer surface of the film by any one of a variety of techniques. Electrodeposition can be used to deposit a metal, e.g. a transition metal such as tin, copper, iron, or silver, at the pore bottoms by the procedure disclosed for example in our British patent specification no. 1,532,235 published on Nov. 15, 1978 (the disclosure of which is incorporated herein by reference). Vacuum sputtering and similar techniques can be used to coat the surface of the film with a continuous or discontinuous layer of metal of any type. Electroless or immersion plating can be used to coat both the surface of the porous layer and the internal walls of the pores with various metals.

A surface metal layer can also be formed by first "flash" anodizing a metal substrate to form a thin non-conductive essentially non-porous oxide layer, depositing a metal layer on the oxide layer by electroless plating and then continuing the porous anodization to grow a porous oxide film below the metal layer and forming the weakened stratum in the porous oxide film. This procedure is feasible if the metal layer is not made too thick, i.e. so that it remains discontinuous or at least porous to the electrolyte.

We have unexpectedly found that, when a metal is deposited in the pores, continued porous anodization can be carried out to lengthen the pores beneath the metal deposit and that the weakened stratum can then be introduced into the film at a final stage of this further anodization. This has the advantage that, when the film is detached from the substrate along the weakened stratum, a layer of oxide separates the newly formed surface of the detached film from the metal deposits in the pores so that the metal is buried within the oxide layer at least on one side of the film. This procedure also ensures that all of the metal deposited within the pores is removed with the oxide film as it is detached from the substrate, which may not always be the case if the metal is deposited within the weakened stratum itself.

The ability to carry out further porous anodization after the deposition of a metal in the pores also opens up the possibility of depositing several metal layers within the porous film separated by strata of the oxide. This is achieved by carrying out a first porous anodization step, depositing a metal in the resulting pores, carrying out a second porous anodization to lengthen the pores, electrodepositing a metal at the pore bottoms (a procedure which turns out to be feasible despite the initial metal deposit in the pores), and repeating the procedure if desired to create further metal layers at even lower levels in the film. As a final step, the weakened stratum is introduced into the film.

Although continued anodization below a metal deposit in the pores has been described in simple terms above, it may require a special procedure to avoid dissolution or dispersion of the initial metal deposit in the acidic electrolyte used for the continued porous anodization. This becomes particularly necessary if the initial metal deposit is formed by electrodeposition because metals which can be deposited in this way tend to dissolve or disperse in acidic solutions. This can be avoided by employing one of three alternative methods, as detailed below.

The first method involves electrodepositing a noble metal seed within the pores of the initial structure. Noble metals (e.g. Pd) are resistant to acid electrolytes used for the subsequent porous anodization but they tend to spread up the sides of the pores as deposition proceeds and this may be disadvantageous if the deposits are desirably to have uniform heights and flat outer surfaces. Therefore, the electrodeposition is carried out just long enough to deposit a small amount of the noble metal. After the subsequent anodization step to lengthen the pores, the structure is subjected to electroless plating. The noble metal deposit acts as a seed for the deposition of the additional metal and the deposit is thus enlarged until it reaches an adequate size for the desired application.

The second method is similar to the first, except that the noble metal seed is enlarged by electroless plating before the anodization to lengthen the pores. This is possible because the metals deposited by electroless plating (e.g. Ni) are resistant to the acids used in the electrolytes required for porous anodization.

A third method is the most preferred. This involves first electrodepositing the normal (so called ANO-LOK ®) metals. These deposits are then protected by providing them with an acid-resistant coating of a noble metal such as Pd or Au by an immersion plating technique (e.g. using a $PdCl_2$ or $AuCl_2$ solution). Immersion plating is somewhat similar to electroless plating but will not continue indefinitely once it has been initiated, thus plating will cease once all the surface sites of the host metal are occupied). Then further anodization can be carried out to lengthen the pores without the deposits being attacked to any substantial extent. This method is the most preferred because it relies on the electrodeposition of normal deposition metals and because it produces a very regular and uniform semi-transparent metal layer in the anodic film, which is desirable in certain applications.

The invention is described in more detail with reference to the accompanying drawings, in which.

The methods described above and some of the resulting intermediate structures are illustrated in simple schematic fashion in FIGS. 1(a) to 1(h).

Figure 1A:
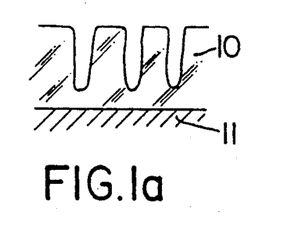
FIGS. 1(a)-(h) show cross-sections of various intermediate structures produced during the process of the present invention.

FIG. 1(a) shows a cross-section of a porous anodic film 10 formed by porous anodizing a metal substrate 11.

Figure 1B:
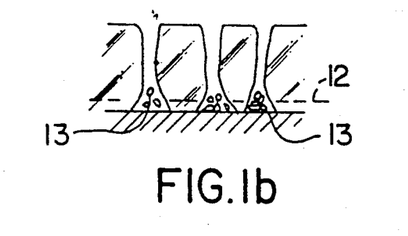

FIG. 1(b) shows the same film after a pore branching step to introduce a weakened stratum 12, formed by branched pores 13, at the substrate/film interface by the collective weakening produced by continuous or stepwise voltage reduction.

Figure 1C:
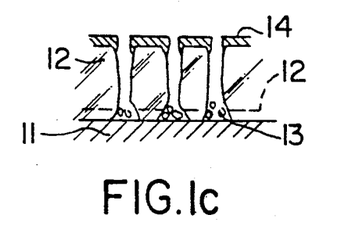

FIG. 1(c) shows the structure of 1(b) having a discontinuous metal layer 14 on the outer surface of the anodic film 10 produced, for example, by sputtering after the formation of the film or by the "flash" anodization procedure described above.

Figure 1D:
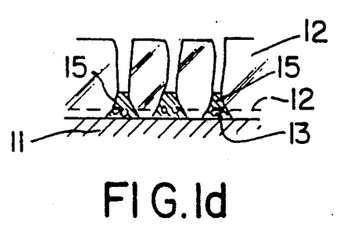

FIG. 1(d) shows the structure of FIG. 1(b) having metal deposits 15 at the bottoms of the pores introduced, for example, by electrodeposition.

Figure 1E:
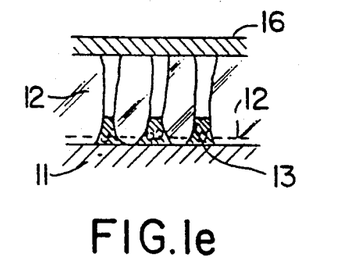

FIG. 1(e) shows a structure similar to FIG. 1(d) having a continuous metal layer 16 on the outer surface of the film formed, for example, by sputtering for a period longer than that required for the structure of FIG. 1(c).

Figure 1F:
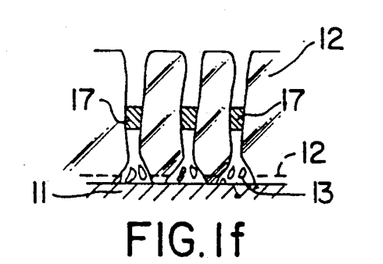

FIG. 1(f) shows a structure having metal deposits 17 at intermediate levels in the pores. These deposits are formed by carrying out a first porous anodization to produce a structure similar to FIG. 1(a), electrodepositing a metal at the bottoms of the pores, carrying out a second porous anodization (after protecting the metal deposits against acid attack, if necessary) to lengthen the pores below the deposits and then carrying out a final pore branching step to create a weakened stratum 12.

Figure 1G:
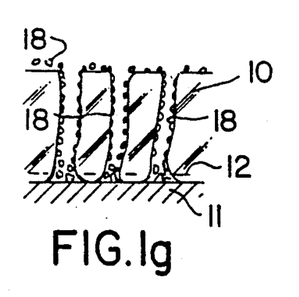

FIG. 1(g) shows a structure similar to FIG. 1(b) having metal deposits 18 coating the surface of the film and the inner walls of the pores. This can be produced by electroless or immersion plating the structure of FIG. 1(b).

Figure 1H:
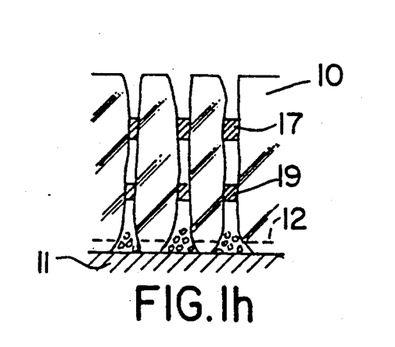

FIG. 1(h) shows a structure similar to FIG. 1(f) except that the metal electrodeposition and pore lengthening steps are carried out a second time to produce additional buried metal deposits 19 before carrying out the final pore branching step. The electrodeposition and pore lengthening steps could be repeated before carrying out the final pore branching step to produce even more buried metal layers, as required. If desired, a surface metal coating (not shown) could then be applied as in FIG. 1(c) or FIG. 1(e).

Further modifications can be employed to produce further intermediate structures if desired. For example the electrodeposits of FIG. 1(d) or FIG. 1(f) may be made to extend to the outer surface of the film by suitably prolonging the electrodeposition or the electroless plating step and may, if desired, merge with a metal surface deposit. Moreover, a structure similar to FIG. 1(g) may be produced with uncoated pore sections at the bottom of the film by carrying out a first porous anodization, electroless plating the resulting film, carrying out a second porous anodization to lengthen the pores (no protection of the deposited metal is usually required because electroless deposited metal is usually resistant to metal attack) and then carrying out the pore branching step.

While the pore branching step is normally carried out as the final step of the electrolysis to position the weakened stratum at the substrate/oxide interface, normal porous anodization can be carried out if desired following the pore branching step in order to separate the weakened stratum from the substrate. This is found to be possible without causing the upper part of the film to detach prematurely and without affecting the ability of the layer to detach when desired. The advantage of separating the weakened stratum from the substrate is that it may give a cleaner separation (fewer defects) if there are localized defects in the film due to the impurities in the substrate.

By combining various steps in various ways, a large variety of intermediate structures can be formed.

Once an intermediate structure of the type shown in FIGS. 1(c) to 1(h) has been formed, the next step is to detach the metal-containing film 10 from the substrate 11 along the weakened stratum 12. If the film is relatively thick and self-supporting, this can be done by allowing the anodic film to stand or "soak" in the acidic electrolyte until it separates at the weakened stratum; but it is more conveniently done by attaching a flexible non-porous or porous support to the outer surface of the film and using the support to peel the film from the substrate. Alternatively, if the substrate 11 itself is flexible (e.g. a metal foil), a relatively inflexible support can be applied to the film and the substrate can be peeled away from the support and the attached metal-containing anodic film 10. This has the advantage that the metal-containing anodic film is not flexed during its detachment from the film and therefore has less tendency to crack or split, an advantage that may be useful for thicker anodic films which tend to be less flexible than very thin films.

The support can be attached to the anodic film by any suitable means. For example, when the support is a polymer sheet it may be adhered or heat sealed (e.g. if made of polypropylene) to the anodic film or metal coating layer. Hot melt interfacing materials can be applied in preprogrammed patterns or designs. This provides a meltable layer between the anodic film and the support. Alternatively, iron-on interfacing, normally used for stiffening fabrics, can be used to attach a membrane, such as a porous nylon mesh, to the anodic film. If a porous support is to be adhered to the anodic film and its porous nature is to be maintained, this may be done by the spot application of adhesive or polymer solution, e.g. using ink jet printing techniques, to prevent complete blocking of the pores. Yet another attachment technique involves so-called heat staking a porous polymeric membrane of polypropylene, if necessary facilitated by the use of a laser.

The support may be inorganic rather than organic (e.g. the polymer mentioned above). For example, the anodic film may be incorporated into a porous composite membrane of the type disclosed in our co-pending British patent application serial number 8912425.9 filed on May 31, 1989, the disclosure of which is incorporated herein by reference. In such a composite, the porous anodic film is integrally bonded to an overlying layer of partly sintered inorganic particles by one of two methods. In the first method, a slurry of inorganic particles is "tape cast" onto the film surface and then heated to partly sinter the particles together. In the second method, a slurry of inorganic particles is tape cast onto the surface, a preformed layer of sintered particles is then applied on top and finally the coatings are heated. In each case the average pore size of the ceramic layer is larger than the average minimum pore size of the metal-containing anodic film.

After detachment of the metal-containing film, the support can be used as a new substrate for the two phase film or it can be subsequently removed or replaced. Removal of the support can be carried out, for example, by sandwiching the laminate of the two-phase film and the support between a pair of fine mesh grids (made for example of TEFLON or stainless steel) and dissolving or burning away the substrate in situ. If the two phase film is sufficiently thick (e.g. greater than about 50 microns) it may not be necessary to continue to support the resulting free-standing laminate with the mesh grids. If the two phase film is very thin, on the other hand, the mesh grids can be used to form a new supporting structure even though they may not be bonded to the film, or a new support may be attached. Alternatively, pores in selected areas of the anodic film may be filled with a material (e.g. a settable liquid such as a lacquer or a polymer solution) that itself reinforces the film. If a suitable pattern of application is selected, such as a dot or grid pattern, good support may be provided while maintaining high average porosity of the film. The material penetrating the pores in this way can act alone as a supporting structure after the original support has been removed or it can provide additional support in combination with a layer of material or other supporting structure.

Incidentally, after detachment of the two phase film 10 from the substrate 11, the exposed lower surface of the film can, if desired, be coated with a discontinuous or continuous layer of a metal, e.g. by sputtering.

The substrate 11 used for the formation and initial support of the porous layer can be of any suitable shape, size and thickness, e.g. a plate, a shaped article, bulk metal, a foil or a thin layer itself supported by another material. If the substrate is a flexible metal foil and if low anodizing voltages are employed for the formation of the film so that the risk of "burning" the foil by heat generation is minimized, the process can be carried out continuously or semi-continuously. For example, the metal foil can be unwound from a roll, passed through a first electrolysis bath to carry out initial porous anodization, passed through a metal deposition station, passed through a further electrolysis bath to introduce a weakened stratum, adhered to a flexible support unwound from a roll and then separated from the support with the separated parts being wound up or processed separately. The metal foil substrate could possibly be reused for economy. The details of the precise steps would of course have to be varied according to the particular structure being formed.

Examples of some of the structures which can be produced in this way or on a batchwise basis are shown in FIGS. 2(a) to 2(m) (omitting any support that may be present). The pores and deposits in these figures are shown in a similar manner to those in FIGS. 1(a) to 1(h) and so detailed explanation is believed to be unnecessary as the structures represented will be self-evident.

The two phase films produced according to the present invention can be used for a variety of applications, most of which fall into three generic areas. First, the invention makes it possible to coat substrates made of non-anodizable materials, e.g. plastic and paper, with metal-containing oxide films (for which direct deposition is problematic) by fabricating the films on anodizable metal substrates and transferring them. Second, if the spacings between the supported metal layers in the films are made optically thin (i.e. thin enough to create light interference, e.g. less than 3 microns and preferably less than 1 micron), the films are capable of generating optical interference effects which can be imported to various supports, e.g. transparent layers of glass or plastic. Optical structures of a similar kind are discussed in our Canadian Patent Application Serial No. 615,000, filed Sept. 29, 1989, the disclosure of which is incorporated herein by reference. Third, it is possible to transfer anodic films loaded with chemically active metals to plastic or to a porous support to make selective active coatings or permeable membranes.

These applications are discussed in more detail below with reference again to the structures of FIG. 2. Incidentally, in the structures as shown in the figure, a support would normally be laminated to the upper surfaces of the structures shown.

An example of the products which can be produced by coating two phase anodic films on a non-metallic substrate is a magnetic recording film. Conventional magnetic media for recording or information storage consist typically of fine magnetic particles, such as iron oxide, dispersed in a polymeric binder media which is spin coated as a thin film onto a rigid disk or applied to a flexible web for magnetic tape or floppy disks. More recently, the use of continuous thin magnetic films vacuum deposited onto a disk or flexible web has been developed. A third type of magnetic media for rigid disks consists of an aluminum platter anodized to provide a porous anodic film over the surface in which magnetic particles such as cobalt are electrodeposited into the pores (see S. Kawai, R. Ueda, J. Electrochem, Soc. 122, 32 (1975)). Recently this type of media has been extended to flexible substrates (see N. Tauya, T. Tokushima, M. Shiraki, Y. Umehara, IEEE Trans. Mag. vol. 24, 1790 (1988) in a process where plastic film such as polyester is vacuum deposited by evaporation with aluminum to a thickness of several microns then anodized and electrodeposited as for rigid media. A disadvantage of this approach is that using a thin film of aluminum initially, and particularly after an appreciable portion of the aluminum is consumed in the anodizing, the residual aluminum cannot support high currents and so the anodizing can only be accomplished at low rates. Additionally, the appreciably greater resistance of the web at its centre relative to the edges, leads to non-uniform anodizing across the width of the web. Moreover, the heat generated due to the resistance of the aluminum film can have a deleterious effect on the porous anodic film, which is sensitive to temperature, and hence on the magnetic properties.

All of these difficulties would be removed by having a much thicker conductive layer of aluminum than is actually needed for the required anodic film thickness, but this would seriously limit the rate of the vacuum deposition stage. Further disadvantages of this approach are the characteristically poor adhesion of aluminum to plastic and the residual aluminum left after anodizing which is susceptible to corrosion in humid environments thus limiting media lifetime.

The present invention can be used to form the anodic film to the required thickness and with magnetic metal (Fe, Ni, Co) deposited in the pores, directly on an aluminum foil substrate. A weakened stratum is incorporated in the film below the metal deposit, as in the structure of FIG. 2(e), to allow transfer on lamination to a flexible web material. Thus the anodization can be carried out at high speed and with excellent uniformity due to the thick conductive foil. The adhesion of the transferred anodic film to the plastic web can be very good. There is no residual aluminum to cause stability problems. On anodizing, a section of continued anodizing film can be left below the deposit and above the weakened stratum to provide a residual porous layer on the top of the transferred structure. This functions as a hard overlayer which additionally can be impregnated with lubricant. It should be noted that the metal deposit in FIG. 2(e) is preferably formed by electroless plating since electrodeposition to the required thickness may tend to block the pores and prevent continued anodization.

There is also a need for packaging that can protect magnetic media, magnetic stripes on credit and identity cards, etc. from stray magnetic fields. Suitable packaging can be made by transferring a metal-containing anodic film, such as the one used for magnetic media described above, onto paper or plastic. Films of this type yielding sufficient magnetization may still be transparent, due to the discrete nature of the deposits, providing greater appeal as a packaging film.

Examples of devices incorporating optical interference films are as follows. Structures such as those shown in FIGS. 2(h) and 2(i) involve a plated metal layer covering one or more semi-transparent buried deposit layers within the film. If the plated layer is a metal such as Ag or Pd and the separations between the various layers are optically thin, then the structures are capable of generating interference colours. The structure of FIG. 2(h) gives an MOMO device (metal-oxide-metal-oxide). Due to interference of light reflected from the various layers, the structure appears coloured and the colour may be dichroic. An example of a more complex film according to FIG. 2(i) has the following layers Pd (opaque)/4.36 L/Pd/4.36 L/Pd where L is aluminum oxide in quarterwaves at a set point of 550 nm (i.e. 3747 Angstroms), and the Pd layers are nominally 50-100 Angstroms thick. This film exhibits a gold-to-green colour shift.

Although the structure of FIG. 2(h) has an electrodeposited (versus electroless) layer which tends to plug the pores, the fact that continued anodization can be carried out below such a deposit indicates that liquids or other materials may penetrate through the deposits and produce colour shifts due to the consequent change of effective refractive index of the film between the reflective layers. Thus, devices of this kind can be used in a variety of devices and sensors which produce a visible colour shift when materials enter or leave the pores. Examples of such devices include moisture sensors, freeze-thaw indicators, etc.

Figure 2A:
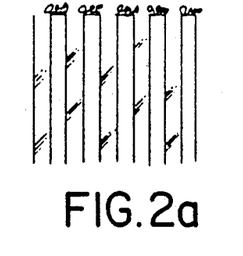
FIGS. 2(a)-(m) show cross-sections of examples of two phase metal/oxide films according to the invention.
Figure 2B:
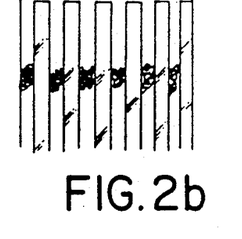
Figure 2C:
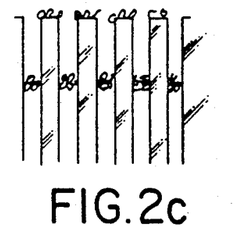
Figure 2D:
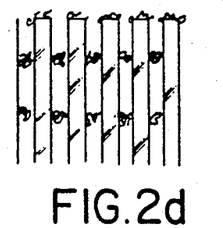
Figure 2E:
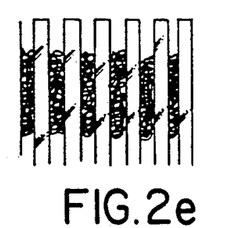
Figure 2F:
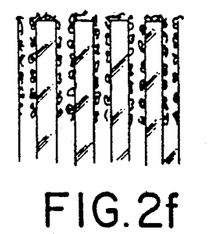
Figure 2G:
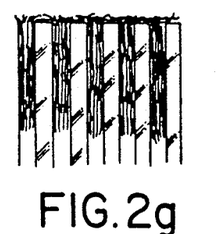
Figure 2H:
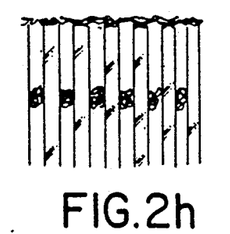
Figure 2I:
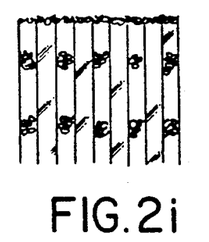
Figure 2J:
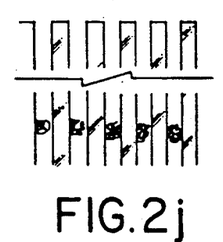
Figure 2K:
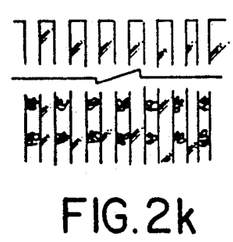
Figure 2L:
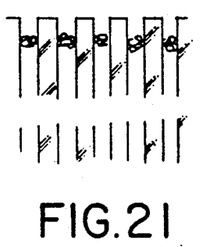
Figure 2M:
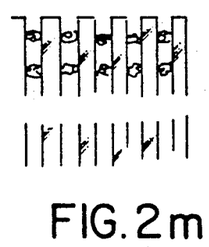
Figure 2N:
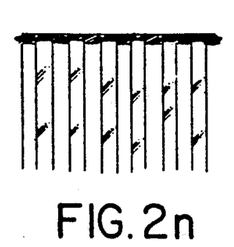

As an alternative to the above procedure, the structure of FIG. 2(b) can be top-metallized by vacuum deposition while intact on the substrate and can then be transferred to yield the same structure as in FIG. 2(h). Alternately, the structure of FIG. 2(b) can be metallized after transfer to a support. These are not preferred routes due to the additional processing but may be more useful for complex structures like those of FIG. 2(i).

In addition the various uses mentioned above, the structures of the present invention may also be used to prepare dichroic pigments, i.e. inks which (when dry) have a colour which exhibits dichroism. Inks of this type are useful for security printing applications because of the inability to copy the dichroic effect. However, a problem is encountered when conventional dichroic structures are used to prepare such pigments because these structures are quite thick compared to the required diameters of particles used for ink (5-10 microns). If the colour and dichroism are to be highly visible, a large number of the particles must be in the proper orientation when the pigment is dry on a suitable substrate, but a large number of thick particles are orientated with the uncoloured side surfaces outermost and so the resulting colours are weak. To overcome this problem, the optical structure, including any support, must be very thin. To be effective, targeted aspect ratios (particle surface diameter:particle thickness) should be at least 5:1. This is difficult to achieve with the conventional structures, but can be achieved in the following way.

Figure 3A:
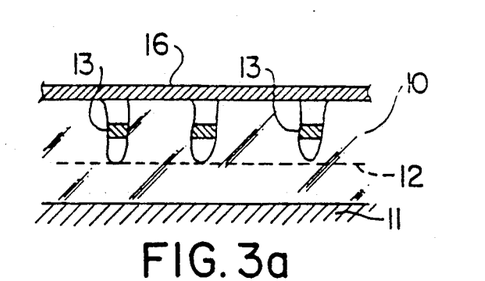
FIGS. 3(a)-3(b) and 4 are cross-sections of structures used to prepare dichroic pigments.
Figure 3B:
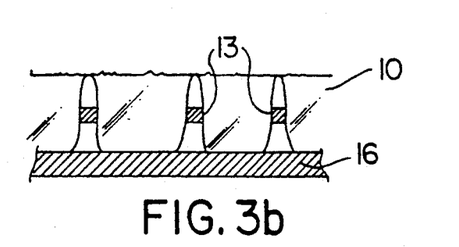
Figure 4:
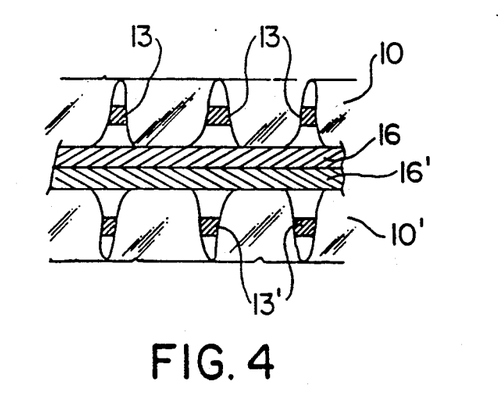

The preparation of such pigments is explained in connection with FIGS. 3(a) and (b) and FIG. 4. FIG. 3(a) shows an intermediate structure similar to that of FIG. 1(e) except for an additional layer of oxide beneath the weakened stratum 12. The outer part of the film can be detached without the intervention of a support by scratching the film since small particles are anyway desired. This provides the structure shown in FIG. 3(b) which is a OMOM device capable of producing a dichroic colour if the spacings between the layers are made suitably thin. Since there is no polymer or other support, and the opaque reflective metal layer 16 is very thin (e.g. if produced by sputtering), the entire particle is very thin, i.e. in the region of 1 micron or less. Flakes having a size of 5-10 microns made from such a film consequently have the desired aspect ratio, and can thus be used to form dichroic pigments.

Even these particles suffer from the problem that about 50% will have the opaque layer 16 outermost and will thus not exhibit interference effects. This disadvantage can be overcome by bonding two of the coated structures of FIG. 3(a) back to back and then detaching the outer layers at the weakened strata to create an ultra thin, cross-sectionally symmetrical (OMOMOMO) structure as shown in FIG. 3 which exhibits the interference effects when either face is uppermost. By using structures of suitable initial thickness, symmetrical structures having a thickness of about 1 micron can be provided.

In addition to the various uses mentioned above, the intermediate structures of the present invention incorporating a weakened stratum may also be used as dichroic hot stamp foils, i.e. foils which when transferred have a colour which exhibits dichroism. Hot stamp foils can be prepared by taking a dichroic structure containing a weakened zone, e.g. according to FIG. 3(a), and applying an adhesive to the metallized surface layer 16. Transfer of the dichroic foil is realized by applying pressure and heat if the adhesive is heat activating) between this structure and the surface on to which the transfer is to be made. The structure of FIG. 3(b) remains on the surface to be coated as the structure shears at the weakened stratum and exhibits a dichroic colour.

All of the interference structures described above are based on reflection which takes place at a reflective lowermost layer of some kind. It is also possible to use the present invention to produce transmission optics, i.e. the structures of FIGS. 2(b), (c) and (d) which approximate to interference filters of the metal/dielectric type. The latter are used routinely in precision optical elements such as lens coatings and a variety of designs with specific materials choices are available for particular pass-band or edge filters.

Figure 5:
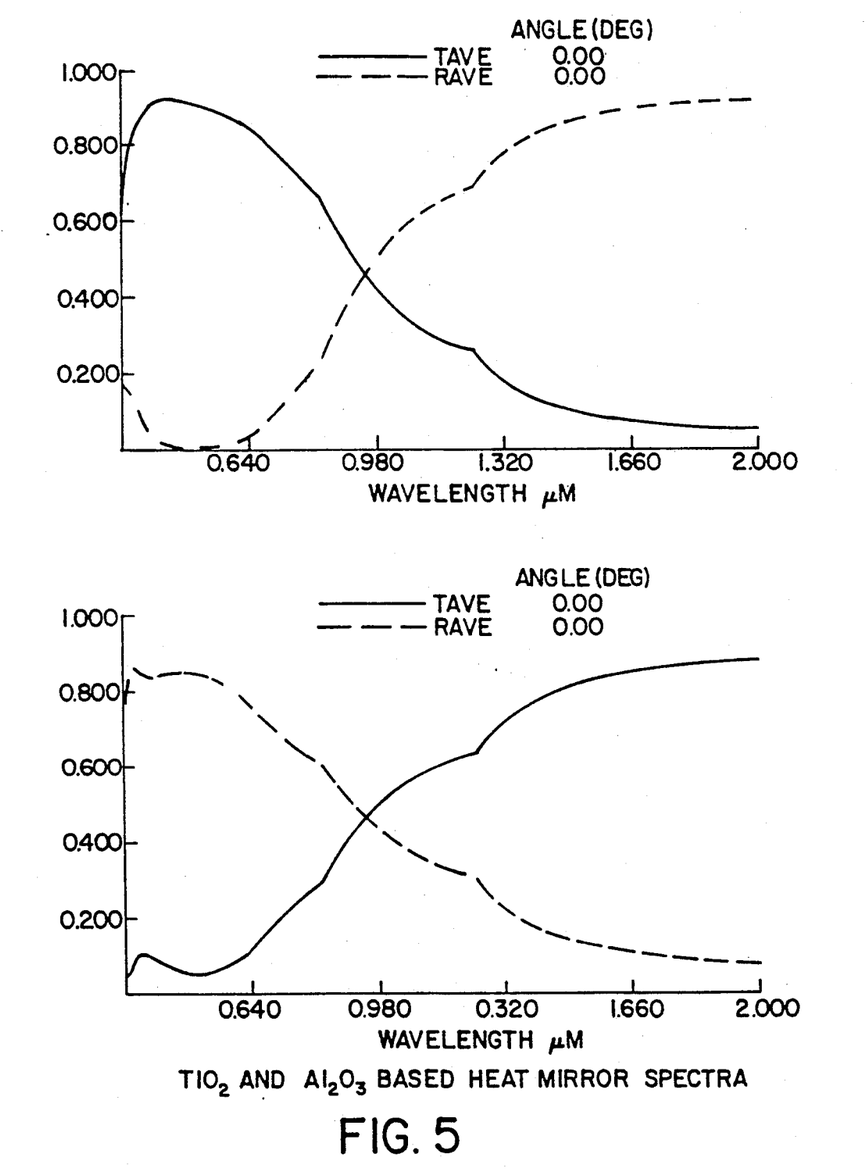
FIG. 5 shows the transmission spectra of a conventional glass coating (top) and a coating comprising a film according to a preferred form of the present invention (bottom)

Application for such devices can be found in the area of solar control film for lamination to windows. One example is a transparent heat-mirror that transmits in the visible and reflects in the infrared region of the spectrum. The accepted optical design (J. C. C. Fan et al., Applied Phys. Lett. 25, 693 (1974)) is a dielectric/metal dielectric structure with $TiO_2$ as the dielectric and Ag as the metal. Such films, deposited by vacuum evaporation, are pervasive in the laminated window industry. FIG. 5 shows the reflectance and transmittance spectra for such a design along with calculated spectra for an $Al_2O_3/Ag/Al_2O_3$ structure designed to match its response. The latter can be realized directly by structure of FIG. 2(b). As expected, the $Al_2O_2$ structure is not as sharp, nor does it have as high a peak transmittance in the visible as the conventional $TiO_2$ structure, but it does have good performance. It is anticipated that there will be cost/performance niches for this anodic coating.

Another application of the present invention is controlled atmosphere packing. This refers to a method for extending the useful life of fresh food by altering the gaseous composition of the atmosphere inside the food package. This technology is presently based on including a packet containing active materials such as gas scavengers, emitters, scrubbers and absorbers inside the package. This approach has limited consumer appeal. In contrast, the present invention can be used to directly incorporate such materials into the plastic of the package using a transferred anodic film as a support or receptacle for these materials. Non-optical structures of the types shown in FIGS. 2(e) and (f) are particularly suitable.

The basic areas presently of interest are:
(a) Oxygen scavengers—these absorb oxygen inside the package thus restricting bacterial respiration and eliminate the need for conventional preservative additives such as BHA in cereals.
(b) Carbon dioxide emitters—these reduce the respiration rate of packaged food. $CO_2$ acts also as a bacteriostat, combining with moisture in the package to form carbonic acid which inhibits growth of bacteria and mould.
(c) Ethylene absorbers—ethylene is emitted naturally by fruits and vegetables as they ripen but causes them to rot as the gas accumulates. Controlling the amount of this gas present thus affects the rate of ripening.
(d) Moisture absorbers—these retard spoilage by reducing microbial activity on the surface of the product.

An example of an oxygen scavenging film would be one containing iron or active iron oxide particles which transform to higher oxides or hydroxides on absorption of oxygen.

One additional feature of the present invention in this field is the ability to activate the anodic film at point of use by peeling off the substrate foil.

The structures of the present invention can also be used as catalysts when catalytically active metals are supported by the anodic film. Moreover, if the metal deposits are porous, the structures can be used as flow-through catalysts which allow the reagents to flow through the anodic film and to contact the catalytically active metal. Structures such as those shown in FIG. 2(a) and (f) with deposits of Pt or Pd are particularly well suited for this purpose.

If metal porous metal layers are deposited on both sides of the oxide film, the resulting structure can be used as a two electrode filter for applying a voltage gradient across the filter.

The invention is illustrated in further detail by the following non-limiting Examples.

EXAMPLE 1

Figure 6:
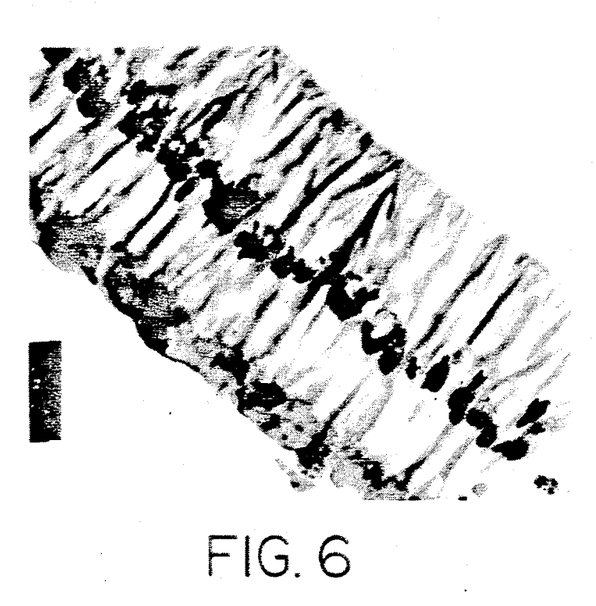
FIG. 6 is a photomicrograph of a structure according to the invention produced according to the Examples below.

Optically variable flakes are prepared by chemically processing aluminum foil to create a poorly adhering porous oxide film containing a buried discontinuous metal layer and subsequently sputter depositing an opaque layer of aluminum on the surface. When the foil is bent around a short radius, flakes of the film pop off. The micrograph of FIG. 6 reveals a highly magnified cross-section of such a flake which shows a 200 nm layer of porous oxide separated from a second 150 nm layer by a 70 nm thick layer of metallic particles. A 100 nm section of aluminum reflector layer can be seen coating the one side of the structure. The layer was prepared as follows.

An 8.5 by 12.5 cm 60 micron thick aluminum/polyester panel was anodized in 1M 30° C. $H_3PO_4$ at 15 volts dc for 270 seconds. It was then rinsed thoroughly and immersed in a Ni ANOLOK TM solution whereupon it was given a 40 second 10 volt ac electrolytic treatment. After rinsing, the panel was immersed in a dilute palladium salt solution for a period of 120 seconds. The panel was then rinsed and re-immersed in the anodizing solution where it was re-anodized as before for 90 seconds. Subsequently, the anodizing voltage was reduced in a stepwise fashion using 300 times 0.05 volt steps each lasting 0.6 seconds. The panel was allowed to soak for 45 seconds at 0 volts potential before rinsing and drying.

It is to be noted that at this point, the oxide-metal-oxide film could be easily peeled off by any of the methods disclosed in the above disclosure (e.g. it could have been hot melt laminated with a flexible porous or non-porous web, etc.) and used in a variety of applications, e.g. as a flow through catalyst, heat reflecting window film, microwave susceptor, controlled atmosphere packaging film, etc.

After drying, 100 nm of aluminum was sputter deposited on to the surface of the structure. As mentioned earlier, flakes of the structure popped off the aluminum substrate when bent around a short radius. An alternative method to release the flakes was to mechanically scratch the surface and subsequently blow off the flakes using pressurized air.

The flakes were optically variable, changing colour from green to red depending on the angle at which they were viewed.

As an alternative to spalling the structure off and using the flakes to form the pigment base of an optically variable ink, the optically variable structure could be easily coated with a heat set adhesive (e.g. Rohm & Haas product B48S) and transferred to paper, wood, plastic, etc. via hot stamping.

EXAMPLE 2

As in Example 1, an optically variable transferable structure was prepared by chemically processing aluminum foil to create a poorly adhering porous oxide film containing a buried discontinuous metal layer and subsequently sputter depositing an opaque layer of aluminum on the surface. This Example differs in that an electroless metal deposition technique is used to form the discontinuous metal layer.

An 8.5 by 12.5 cm 60 micron thick aluminum/polyester panel was anodized in 1M 30° C. $H_3PO_4$ at 15 volts dc for 240 seconds. The anodized panel was then rinsed thoroughly and immersed in a dilute palladium nitrosyl-sulfate solution at pH 2.0, whereupon it was given a 20 second 10 volt ac electrolytic treatment. After rinsing, the panel was immersed in an electroless Ni solution (Harshaw Chemical Co. Alpha 103) maintained at 73° C. for a period of 20 seconds. The panel was then rinsed and re-immersed in the anodizing solution where it was re-anodized as before for 90 seconds. Subsequently, the anodizing voltage was reduced in a stepwise fashion using 300 times 0.05 volt steps each lasting 0.6 seconds. The panel was allowed to soak for 45 seconds at 0 volts potential before rinsing and drying.

It should by noted that at this point, the oxide-metal-oxide film could by easily peeled off via any of the methods disclosed in the above disclosure (e.g. it could have been hot melt laminated with a flexible porous or non-porous web, etc.) and used in a variety of applications, e.g. as a flow through catalyst, heat reflecting window film, microwave susceptor, controlled atmosphere packaging film, etc.

After drying, 200 nm of aluminum was sputter deposited on to the surface of the structure. As mentioned earlier, flakes of the structure popped off the aluminum substrate when bent around a short radius. An alternative method to release the flakes was to mechanically scratch the surface and subsequently blow off the flakes using pressurized air.

The flakes were optically variable, changing colour from purple to yellow depending on the angle at which they were viewed.

As an alternative to spalling the structure off and using the flakes to form the pigment base of an optically variable ink, one could easily coat the structure with a heat set adhesive (e.g. Rohm & Haas product B48S) and transfer the optically variable structure to paper, wood, plastic, etc. via hot stamping.

EXAMPLE 3

In this Example, the buried metallic layer is prepared by first seeding the film with a metallic precursor and subsequent to re-anodizing an electroless technique is used to plate the metal at the location of the seed.

A 4 by 12 cm 60 microm thick aluminum/polyester panel was anodized in 1M 30° C. $H_3PO_4$ at 15 volts dc for 210 seconds. It was then rinsed thoroughly and immersed in a dilute palladium nitrosyl sulfate solution whereupon it was given a 10 second 15 volt ac electrolytic treatment. The panel was then rinsed and re-immersed in the anodizing solution where it was re-anodized at 15 volts dc for 90 seconds. Subsequently, the anodizing voltage was reduced in a stepwise fashion using 300 times 0.05 volt steps each lasting 0.6 seconds. The panel was allowed to soak for 45 seconds at 0 volts. The final stage included building up the metallic seed deposit via immersion in an electroless nickel solution for a period of 15 seconds (Harshaw Chemical Co. Alpha 103) at 80° C. followed by rinsing and drying.

At this point, the oxide-metal-oxide film could be easily peeled off via any of the methods disclosed in the above disclosure (e.g. it could have been hot melt laminated with a flexible porous or non-porous web, etc.) and used in a variety of applications, e.g. as a flow through catalyst, a heat reflecting window film, a microwave susceptor, a controlled atmosphere packaging film, etc.

We claim:

1. A process of producing a two phase metal/oxide film, which comprises:
    forming a porous oxide film on a substrate,
    introducing a weakened stratum into the oxide film so that at least an outer part of the film can be subsequently detached along said stratum,
    depositing a metal on and/or within the pores of said film in at least said outer film part, and
    detaching at least said outer film part from said substrate;
    wherein at least said outer film part is detached by attaching a flexible support to said anodic film and peeling said support from said substrate.

2. A process of producing a two phase metal/oxide film, which comprises:
    forming a porous oxide film on a substrate,
    introducing a weakened stratum into the oxide film so that at least an outer part of the film can be subsequently detached along said stratum,
    depositing a metal on and/or within the pores of said film in at least said outer film part, and
    detaching at least said outer film part from said substrate;
    wherein said substrate is flexible and wherein at least said outer film part is detached by attaching an inflexible support to said anodic film and peeling said substrate from said support.

3. A process according to claim 1 or claim 2 wherein said support is subsequently removed from said outer part of said film.

4. A process according to claim 1 or claim 2 wherein said support is subsequently replaced by another support.

5. A process of producing a two phase metal/oxide film containing metal deposits positioned between inner and outer ends of pores in said film, which process comprises:
- carrying out a first porous anodization of an anodizable metal substrate to form an initial porous oxide film layer on said substrate;
- depositing a metal at inner ends of pores in said initial porous oxide film layer to form metal deposits in said film layer;
- carrying out a second porous anodization step to form an additional layer of porous oxide film below said initial layer and to lengthen said pores;
- introducing a weakened stratum into said additional porous layer at inner ends of said lengthened pores; and
- detaching said initial and said additional porous film layers containing said metal deposits from said metal substrate along said weakened stratum.

6. A process according to claim 5 wherein said metal is protected against attack by acid before said second porous anodization is carried out.

7. A process according to claim 6 wherein said metal is protected by coating with an acid resistant metal by a process selected from the group consisting of electroless plating and immersion plating.

8. A process according to claim 5 wherein said metal deposited by said electrodeposition is in the form of acid resistant seeds and, following the introduction of said weakened stratum, said seeds are increased in size by electroless plating.

9. A process according to claim 5 for forming a plurality of deposits in said pores between the inner and outer ends thereof which comprises repeating said electrodeposition and porous anodization steps at least once after said second porous anodization step but before the introduction of said weakened stratum.

10. A two phase metal/oxide film comprising a porous oxide film having a metal deposited on a surface of said film and/or within pores in said film to form a plurality of strata of deposited metal, said film being capable of generating an interference colour by reflections from said metal deposits.

* * * * *